United States Patent [19]

Fellman et al.

[11] 4,433,958

[45] Feb. 28, 1984

[54] PERMANENT DENTAL RESTORATIVE MATERIAL

[75] Inventors: Robert P. Fellman, Langhorne; Marvin J. Hurwitz, Elkins Park; Robert M. Myers, Holland, all of Pa.; Gerald F. Slack, Vincentown, N.J.

[73] Assignee: Rohm and Haas Company, Philadelphia, Pa.

[21] Appl. No.: 411,778

[22] Filed: Aug. 26, 1982

Related U.S. Application Data

[63] Continuation-in-part of Ser. No. 305,417, Sep. 25, 1981, abandoned, which is a continuation-in-part of Ser. No. 128,010, Mar. 7, 1980, abandoned.

[51] Int. Cl.$^3$ ................................................. A61K 6/08
[52] U.S. Cl. ...................................... 433/199; 106/35; 260/998.11; 433/201; 433/202; 433/219; 433/223; 433/228; 523/115; 523/116; 523/117
[58] Field of Search .................... 260/998.11; 106/35; 433/228, 199, 219, 223, 201, 202; 523/115, 116, 117

[56] References Cited

U.S. PATENT DOCUMENTS

| | | | |
|---|---|---|---|
| 2,558,139 | 6/1951 | Knock et al. | 523/115 |
| 3,647,498 | 3/1972 | Dougherty | 117/8 |
| 3,923,740 | 12/1975 | Schmitt et al. | 106/35 |
| 4,197,234 | 4/1980 | Temin | 260/998.11 |
| 4,288,221 | 9/1981 | Engel | 433/199 |
| 4,302,376 | 11/1981 | Walkowiak et al. | 106/35 |
| 4,340,532 | 7/1982 | Lee et al. | 433/217 |

FOREIGN PATENT DOCUMENTS 982814 2/1965 United Kingdom .

*Primary Examiner*—Lorenzo B. Hayes
*Attorney, Agent, or Firm*—Jordan J. Driks

[57] ABSTRACT

Wear-resistant, high compressive strength permanent dental restorations are prepared from novel compositions comprising (a) a liquid monomer system comprised of one or more monoethylenically unsaturated monomers and one or more polyethylenically unsaturated monomers, (b) a solid particulate system insoluble in the liquid monomer system (a) comprised of a mixture of both organic and inorganic particulate substances, and (c) a free radical initiator system.

28 Claims, No Drawings

PERMANENT DENTAL RESTORATIVE MATERIAL

This application is a continuation-in-part of Ser. No. 305,417, filed Sept. 25, 1981, now abandoned, which is a continuation-in-part of Ser. No. 128,010, filed Mar. 7, 1980, now abandoned.

BACKGROUND OF THE INVENTION

1. Field of the Invention

This invention relates to the composite dental restorative material art, and to permanent dental restorations made from such materials.

2. Description of the Prior Art

Compatability of Various Materials with Oral Tissues, I: The Components in Composite Restorations. Bowen, J. Dent. Res. 58 (5): 1493-1503, May 1979, summarizes the current status of the art with respect to composite restorative materials used for dentistry.

U.S. Pat. No. 4,197,234, Temin is directed to dental restorative compositions. The '234 patent discloses a dental restorative composition which includes an acrylic monomer, a fluorinated polymer as a filler, and other filler materials. The fluorinated polymer is present in an amount of from about 1% to 10% of the total amount of filler. The dental restorative composition of the '234 patent, although an advance in the art, still suffered from the disadvantage that, dental restorative materials prepared from the '234 compositions exhibited poor wear resistance thereby rendering them undesirable for prolonged use in the mouth of a patient.

SUMMARY OF THE INVENTION

It is one object of the present invention to provide compositions useful for preparing permanent dental restorations having high compressive strength and wear resistance.

It is another object of the present invention to provide methods for making such permanent dental restorations and to provide the restorations themselves. Another object of the present invention is to provide compositions for preparing permanent dental restorations which can be cast in a dental office in a short period of time, or in a dental laboratory. A still further object is to provide permanent dental crowns having minimum compressive strengths of at least 20,000 psi and preferably at least 30,000 psi, and rotary wear values of at least 200 hours/mil.

These objects, and others as will become apparent from the following description, are achieved by the present invention which in one aspect is a composition comprising (a) about 10 to 60 parts by weight of a liquid monomer system comprised of one or more monoethylenically unsaturated monomers and about 10% to 80% by weight, based on liquid monomer system, of one or more polyethylenically unsaturated crosslinking monomers; (b) about 40 to 90 parts by weight of a solid particulate system comprised of a mixture of both organic and inorganic particulate substances, each of said substances being insoluble in said liquid monomer system, wherein the weight ratio of the organic particulate substance to inorganic particulate substance is from about 2:1 to about 10:1 respectively and (c) a free radical initiator system. In another aspect, the invention comprises permanent dental restorations having high compressive strength and wear resistance cast from such compositions, and to methods of making such permanent dental restorations comprising mixing the liquid monomer system, the solid particulate system, and the components of the free radical initiator system, filling a mold with the mixture, allowing the composition to set, and then to cure.

DETAILED DESCRIPTION OF THE INVENTION AND THE PREFERRED EMBODIMENTS

When used herein, the term "permanent" means long lasting, as opposed to temporary dental restorations. Temporary restorations are only designed to last six months or less, whereas the restorations of the invention are designed to last for the life of the patient, although these "permanent" restorations can be removed by a dentist if necessary. The term "restorations" refers to crowns, bridges, fillings, repairs to damage caused by trauma; repairs to existing crowns, and cosmetic repair in general. "Restorative material" refers to material used for such restorations. The term "crown" refers to the whole tooth surface rather than selected portions thereof.

The solid particulate system is comprised of the mixture of both organic polymeric and inorganic substances, each of said substances being insoluble in the liquid monomer system. The organic polymeric particulate substance which is used should have a coefficient of friction such that the final dental restorative has a coefficient of friction of not greater than 0.3. Although an organic polymeric substance may be used which results in a final dental restorative product having a coefficient of friction in excess of 0.3, such higher coefficient of friction will, when used, result in a dental restoration having a reduced wear resistance. Among the preferred organic polymeric particulate substances which may be used are those which are fluorinated, for example poly(ethyleneco-chloro-trifluoroethylene), poly(vinylidene fluoride), and the like. Other organic polymeric particulate substances such as polyacetal, various nylons such as nylon 6, nylon 610, nylon 66, and nylon 11 are also suitable, but are less preferred.

When the composition is to be used to cast a restorative material such as a dental crown, it is preferred that the inorganic particulate substance used should comprise at least about 97% by weight of the total inorganic substance, of a material which has a Moh hardness of up to about 5. If the Moh hardness of more than 3% of the inorganic substance substantially exceeds 5, then the final dental restoration such as a crown, will be too abrasive and will result in excess wear of the opposing tooth surface.

Among the inorganic particulate substances which have a Moh hardness of up to about 5 are hydroxyapatite, stearate-coated calcium carbonate, calcium carbonate generally, calcium metasilicate, talc, clay, calcium sulfate, and combinations of any of the aforementioned inorganic substances can be used.

The following inorganic particulate substances have a Moh hardness which exceeds 5. This other class of inorganic particulate substances may be present in an amount of up to about 3%, based on the weight of total inorganic particulate substance present, when the final dental restorative is to be used as a crown or bridge (total dental restorative), and the like. However, when the final dental restorative is to be used as a filling, inlay, (partial dental restorative) and the like, up to about 80%, by weight of the inorganic particulate substance may have a Moh hardness in excess of 5. Among the inorganic particulate substances having a Moh hardness in excess of 5 which may be used are quartz, silica, glass beads, glass fibers and the like.

About 40 to 90 parts, by weight, of the solid particulate system (inorganic plus organic) is used with about 10 to 60 parts of the liquid monomer system. The preferred amount of solid particulate system is about 50 to 70 parts by weight. The particle size of the inorganic particulate substance is about 0.1 micron to about 75 microns and the particle size of the organic polymeric particulate substance is about 0.1 micron to about 75 microns. The weight ratio of organic polymeric particulate substance to inorganic particulate substance is about 2:1 to about 10:1 broadly, and about 4:1 to about 8:1 preferably. Further, optional ingredients such as tinting agents, stabilizers to control polymerization rate, exotherm, and yellowing, fluorescing agent, x-ray opacifying agent, and the like, can be included in either component.

In addition to the aforementioned organic polymeric particulate substance and the inorganic particulate substance, when a putty-like consistency of the uncured restorative material is desired, we have found it helpful to add as part of the organic particulate material, either suspension or emulsion prepared polymers in bead form or finely ground dental restorative resin, or both.

The polymers in bead form are typically prepared by suspension polymerization in an aqueous medium as described by C. E. Schildknecht, *Vinyl and Related Polymers*, 211–214, J. Wiley & Sons, 1954. The beads should pass through a 200 mesh screen and have an average particle diameter in the range of about 1 to 75 microns. Examples of suitable suspension polymer beads are polymethyl methacrylate or polyethyl methacrylate having average particle diameters in the range from about one micron to about 75 microns. Crosslinked or non-crosslinked beads may be used.

The finely ground dental restorative resin is typically the cured system of the invention, finely ground, and added back to the uncured system. Uncrosslinked regrind may also be used.

About 10 to 75 parts by weight, based on final composition, of the suspension polymer in bead form or the finely ground crosslinked or non-crosslinked dental restorative resin or both are normally suitable. About 20 to 50 parts by weight, based on final composition, are preferred.

The free radical initiator system may be any free radical initiator system such as a thermal initiator, a photochemical initiator or a redox initiator and the like.

The thermal initiator may be any thermal initiator such as a peroxydicarbonate, an azo initiator such as azoisobutyronitrile and the like. The thermal initiator is dispersed in the solid portion of the composition and may be used, as the free radical initiator system, when polymerization of the composition is to take place either inside or outside the patient's mouth.

The photochemical initiator may be any photochemical initiator such as the aliphatic ethers of benzoin (particularly the methyl ether), alpha methoxydioxybenzoin, an alpha-diketone (particularly dl-camphoroquinone) and the like. Additionally, a polymerization accelerator, such as a tertiary aliphatic amine (particularly triethanolamine) may also be present. The photochemical initiator may be dispersed in either the liquid monomer system or the solid phase of the composition, or, if the photochemical system is composed of more than one component, said components may be dispersed so that one or more component(s) is in the liquid monomer system and the other component or components is in the solid phase of the composition. The use of photochemistry, as applied to dental materials is described in Polymer Science and Technology, Vol. 14, (Biomedical and Dental Applications of Polymers), entitled "The Application of Photochemistry To Dental Materials," pages 411–417, R. J. Kilian (1981).

If a thermal or photochemical free radical initiator system is to be used, then such initiator system is present in an amount of from about 0.01 part to about 2.0 parts, by weight, per 100 parts of liquid monomer system and preferably, if photochemical, from about 0.1 to about 1.0 part by weight, as aforesaid and if thermal, preferably from about 0.5 to about 2 parts by weight, as aforesaid.

The redox initiator system which may be used is added to the composition in a manner such that the oxidizing agent is kept separate from the reducing agent until the liquid monomer phase is mixed with the solid phase. This may be accomplished by adding the reducing agent to the liquid monomer system and the oxidizing agent to the solid phase. The liquid monomer system is kept separate from the solid phase until it is desired to use the composition, at which time the liquid monomer system is mixed with the solid phase. Other methods of avoiding premature redox initiation of the composition will be apparent to one skilled in the art.

Although a wide range of redox initiator systems are known in the art and are suitable, a particularly suitable system is a combination of benzoyl peroxide and N,N-bis-(hydroxyethyl)-p-toluidine. Other suitable combinations are described by J. M. Antonucci et al., in J. Dent. Res., 58 (9), 1887–99. Suitable amounts of redox pair to be used are about 0.5 to 10 parts by weight, preferably about 1 to 5 parts by weight, per 100 parts of the total composition (liquid monomer system plus solid phase). The redox pair consists of an oxidizing agent and reducing agent. In practice, it is preferred to include the oxidizing agent with the solid phase (organic particulate substance plus inorganic particulate substance) as one component, and the reducing agent with the liquid monomer system as a second component.

The liquid monomer system is comprised of about 10 to about 60 parts by weight of one or more monoethylenically unsaturated monomers and about 10 to 80% by weight, preferably about 20% to about 80% by weight, based on liquid monomer system, of one or more polyethylenically unsaturated crosslinking monomers.

If the crosslinking monomer is present in an amount of less than 10% by weight, then the polymerized composition will have reduced wearability and compressive strength. If the crosslinking monomer is present in an amount of more than 80%, as aforesaid, then the polymerized composition will tend to be brittle.

The liquid monomer system will generally contain at least about 70%, by weight of said monomer system, of an acrylic monomer and preferably at least 95%. of acrylic monomer. The term "acrylic monomer" as used in the specification and claims includes acrylic and methacrylic monomers as well as the vinyl aromatic monomer, styrene.

The monoethylenically unsaturated monomer is selected from the group consisting of those having homopolymer glass temperatures of from about 50° C. to about 120° C., with about 65° C. to about 110° C., preferred. Examples of such monomers and their homopolymer glass temperatures (°C.) are methyl methacrylate (105), ethyl methacrylate (65), isopropyl methacrylate (81), tertiary-butyl methacrylate (107), acrylic acid (103), acrylonitrile (96), sec. butyl methacrylate (60), cyclohexyl methacrylate (75), phenyl methacrylate (112), chlorotrifluoroethylene (52) and styrene (100). Preferred are methyl methacrylate and ethyl methacrylate. If more than one such monomer is chosen, the calculated glass temperature of each monomer need not be within that range, but that of the uncrosslinked copolymer should be within such a range. The calculated glass temperature of the hypothetical uncrosslinked copolymer of the two or more monoethylenically unsaturated monomers employed is determined by the Fox equation as described in S. Loshaeck, T. G. Fox, Bull. Amer. Phys. Soc. 1, (3), p. 123 (1956); as follows, with Tg expressed in °Kelvin:

$$\frac{1}{Tg \text{ (copolymer)}} = \frac{\text{wt. fract. of Monomer } A}{\text{homopolymer } Tg \text{ (Monomer } A\text{)}} + \frac{\text{wt. fract. of Monomer } B}{\text{homopolymer } Tg \text{ (Monomer } B\text{)}} + \frac{\text{wt. fract. of Monomer } N}{\text{homopolymer } Tg \text{ (Monomer } N\text{)}}$$

Monomers which can be used along with other monomers but not as the sole monoethylenically unsaturated monomer are, for example, methyl acrylate (8), methyl acrylate (−22), isopropyl acrylate (−5), n-butyl acrylate (−54), isobutyl acrylate (−43), sec. butyl acrylate (−20), tert-butyl acrylate (41), cyclohexyl acrylate (15), n-octyl acrylate (−35), n-propyl methacrylate (35), n-butyl methacrylate (20), isobutyl methacrylate (48), methacrylic acid (230), vinyl acetate (29), hydroxyethyl methacrylate, octafluoropentyl methacrylate, hexafluoroisopropyl methacrylate, pentafluoropropyl acrylate, pentafluoropropyl methacrylate, heptafluorobutyl acrylate, ethylene, and heptafluorobutyl methacrylate.

An example of such a combination of monomers is a 65:35 ratio, by weight, of n-propyl methacrylate and methacrylic acid, which has a calculated copolymer glass temperature of 83° C.

The amount and type of polyethylenically unsaturated monomer is selected so as to achieve curing in the desired length of time (up to about 20 minutes and preferably up to about 10 minutes), to control exotherm temperature, and to synergistically contribute to the wear resistance and compressive strength of the resultant permanent dental restoration. The preferred polyethylenically unsaturated monomers are polyfunctional acrylates or methacrylates or mixtures thereof and are preferably selected from the group consisting of trimethylolpropane trimethacrylate, 2,2-bis-4-(2-hydroxy-3-methacryloxypropoxy)phenylpropane (bis-GMA), divinylbenzene, diallyl maleate, ethylene glycol dimethacrylate, diethylene glycol dimethacrylate, triethylene glycol dimethacrylate, higher polyethylene glycol dimethacrylates, butylene glycol dimethacrylate, 1,6-hexanediol dimethacrylate, 1,10-decamethylene glycol dimethacrylate, butylene diacrylate, pentaerythritol tetraacrylate, and ethoxylated bis-phenol-A-dimethacrylate.

The composition may also include a thickener polymer dissolved in the liquid monomer system. Such thickener polymer can be any polymer soluble in the liquid monomer system, for example, $C_1$ to $C_4$ alkyl esters of acrylic acid and methacrylic acid. Alternatively, thickeners insoluble in the liquid monomer system such as very finely divided hydrophobic silicon dioxide may be included.

The permanent dental restorations of the invention have a combination of high compressive strength (20,000 psi) and wear resistance (200 hours/mil) never before achieved in the prior art, and are competitive with amalgam, gold, or crown grade porcelain. The restorations to which this invention is most applicable are crowns and bridges, especially crowns.

The method of making the permanent dental crowns of the invention is generally to mix the liquid monomer system, the solid particulate system, and the free radical initiator system, fill a tooth-shaped mold with the mixture, and apply the filled mold to the tooth which has been prepared to receive a crown. If the free radical initiator system used is a redox initiator system, it is important to keep the reducing agent and oxidizing agent separated until the composition is mixed at the time of use. The composition can be in the form of two pastes, a paste and a powder, a paste and a liquid, or a powder and a liquid. The composition is allowed to set, and then to cure. A preferred method comprises (I) mixing (A) a first component comprising about 10 to 60 parts by weight of a liquid monomer system comprised of one or more monoethylenically unsaturated monomers, about 10% to about 80% by weight, based on liquid monomer system, of a polyethylenically unsaturated crosslinking monomer(s), and a small amount of a reducing agent (if a redox initiator is used) with (B) a second component comprising about 40 to about 90 parts by weight of a solid particulate system comprised of a mixture of both organic polymeric and inorganic particulate substances, both of said substances being insoluble in the first component, and an oxidizing agent (if a redox initiator is used), (II) allowing the resultant mixture to achieve a suitable viscosity, (III) filling a tooth shaped preformed mold or impression tray with the thickened mixture, (IV) applying the filled mold or tray to the prepared tooth to which the crown is to be applied, (V) allowing the composition to set, (VI) removing the set crown from the mouth and then from the mold or impression tray, (VII) finishing and polishing the cured crown, (VIII) filling the crown with dental cement and placing the dental crown on the prepared tooth.

In one embodiment of this invention, the aforedescribed method may be practiced using from about 25 to about 60 parts by weight, of a liquid monomer system which comprises one or more monoethylenically unsaturated monomers, such as methyl methacrylate, and about 15% to about 50%, by weight, based on said liquid monomer system, of a polyethylenically unsaturated crosslinking monomer. The solid phase of this embodiment of this invention comprises about 40 to about 75 parts by weight of a mixture of (1) organic polymeric particulate substance which is insoluble in the liquid monomer system and (2) an inorganic particulate substance insoluble in the liquid monomer system. The weight ratio of the organic particulate substance to the inorganic particulate substance is from about 2:1 to about 10:1. The inorganic particulate substance which is used may be one or more of hydroxyapatite, calcium carbonate, stearate coated calcium carbonate, calcium silicate, calcium metasilicate, talc, clay, and calcium sulfate as well as one or more of the above with glass beads, quartz, silica, and glass fibers. The composition also includes a free radical initiator system such as a redox initiator system.

The temperature rise during the setting is generally below 15° C. thereby avoiding discomfort to the patient, and is preferably within the range of 5° to 10° over a set time of about 5 to 15 minutes.

It is preferred that the crown be prepared in a dental office by applying the composition to the prepared tooth and allowing it to set, then curing the crown outside the mouth by applying heat at about 70° C. to about 140° C. for about 15 to 30 minutes, then applying dental luting cement to the inside of the crown, then reapplying the crown to the prepared tooth. An alternative method is to leave the crown on the prepared tooth until it sets, and then allow it to cure in place without removing it. Another method is to send a mold of the prepared tooth to a dental laboratory where the crown is made from the composition of the invention at the laboratory, then having the dentist at a later time apply luting cement to the prepared tooth of the crown and affix the crown to the prepared tooth.

The following specific examples are presented to illustrate a few embodiments of the invention, but it is to be understood that the invention is not limited thereto.

EXAMPLE 1

Test specimens are prepared by mixing in a capsule which is placed in a Vari-Mix ® high speed shaker, 42 parts, by weight, of the liquid monomer system containing the reducing agent and 58 parts of the mixture of organic polymeric particulate substance insoluble in the liquid monomer system and inorganic particulate substance insoluble in the liquid monomer system. The mixture of organic and inorganic particulate substances also contains the oxidizing agent. The test specimens are mixed, in the Vari-Mix ® high speed shaker for 20 seconds. Thereafter, the mixture is poured into a disc-shaped mold, allowed to set at 37° C. and is then cured for 10 minutes at 80° C. and for an additional 20 minutes at 140° C. The liquid monomer system has the following composition:

| Material | Parts by Weight |
|---|---|
| Methyl Methylacrylate | 60 |
| Trimethylolpropane Trimethacrylate | 40 |
| Tinuvin P (a benzotriazole) | 0.10 |
| N,N—bis-(2-hydroxyethyl)-p-toluidine | 0.35 |

The mixture of organic and inorganic particulate substances has the following composition:

| Material | Parts by Weight |
|---|---|
| Crosslinked regrind* | 28 |
| Polyvinylidene fluoride | 16 |
| Crosslinked beads** | 14 |
| Uncrosslinked regrind*** | 1.5 |
| Stearate coated calcium carbonate | 0.6 |
| Calcium metasilicate | 1.7 |
| Benzoyl peroxide (98%) | 1.75 |
| Di-(2-phenoxyethyl) peroxy-dicarbonate | 0.75 |

*The crosslinked regrind has the following composition, in parts by weight: 42 methyl methacrylate, 28 trimethylolpropane trimethacrylate, 12 polyvinylidene fluoride, 18 stearate coated calcium carbonate. The crosslinked regrind is made by a bulk casting polymerization procedure and is granulated and pulverized. The crosslinked regrind which is used is that which passes through a 325 mesh screen.
**Crosslinked beads have the following composition, in parts by weight: 60 methyl methacrylate, 40 trimethylolpropane trimethacrylate. The crosslinked beads are made by emulsion polymerization and are isolated by spray drying, followed by washing and are then dried in vacuo at 125° C. The crosslinked beads which are used are those which pass through a 325 mesh screen.
***Uncrosslinked regrind has the same composition as the crosslinked regrind except that the 28 parts of trimethylolpropane trimethacrylate is replaced with an equivalent amount of methyl methacrylate.

Small cylindrical samples are prepared, in the manner set forth in this Example, by pouring the mixed composition into a cylindrical mold which measures ½ inch in height and ¼ inch in diameter. The resultant compositions are tested for wear life and compressive strength.

The wear life test consists of rotating a cast disc sample under an off-center ceramic scriber having a cylindrical tip 60 mils in diameter under a load of one kilogram/mm$^2$ at 27 rpm for 64,800 revolutions. The test is conducted at 37° C. with continuous water washing. Reference to this test may be found in Powell, J. M., and Dickson, G., J. Dent. Res. 54 (special Issue A) 134 (1975).

The compressive strength test is conducted in accordance with ASTM D-595 and consists of presoaking a rod having a diameter of ¼ inch and a length of ½ inch, in water, for 24 hours and at a temperature of 37° C. The compressive strength is measured immediately after removal of the rod from the water and the test consists of crushing a rod, along its length at a rate of 0.05 in./min.

EXAMPLE 2

Example 1 is repeated except that the liquid monomer system used is 80 parts by weight of ethyl methacrylate and 20 parts by weight of trimethylolpropane trimethacrylate.

EXAMPLE 3

Example 1 is repeated except that the liquid monomer system used is 90 parts by weight of ethyl methacrylate and 10 parts by weight of trimethylolpropane trimethacrylate.

EXAMPLE 4

Example 1 is repeated except that the liquid monomer system used is 12 parts by weight of methyl methacrylate, 8 parts by weight of ethyl methacrylate and 80 parts by weight of triethylene glycol dimethacrylate.

EXAMPLE 5

Example 1 is repeated except that the liquid monomer system used is 60 parts by weight of bis-GMA and 40 parts by weight of triethylene glycol dimethacrylate.

EXAMPLE 6

Example 1 is repeated except that the liquid monomer system used is 60 parts by weight of ethyl methacrylate and 40 parts by weight of triethylene glycol dimethacrylate.

EXAMPLE 7

Example 1 is repeated except that the liquid monomer system used is 36 parts by weight methyl methacrylate, 24 parts by weight ethyl methacrylate and 40 parts by weight of triethylene glycol dimethacrylate.

EXAMPLE 8

This example demonstrates the importance of the range of organic particulate substance to inorganic particulate substance. Example 7 is repeated except that the polyvinylidene fluoride used in the particulate system is replaced with an equivalent amount of calcium hydroxyapatite so that the weight ratio of organic particulate substance to inorganic particulate substance is 1 to 6.

EXAMPLE 9

Example 7 may be repeated and the polyvinylidene fluoride used in the particulate system may be replaced with a 1:1 mole ratio copolymer of ethylene and chlorotrifluoroethylene.

EXAMPLE 10

The procedure of Example 7 may be repeated and the polyvinylidene fluoride may be replaced with nylon 66.

EXAMPLE 11

The procedure of Example 7 may be repeated and the monomer-particulate substrate ratio may be changed to 50 parts of liquid monomer system and 50 parts of the mixture of organic polymeric substance and inorganic polymeric substance.

EXAMPLE 12

Example 1 may be repeated and the liquid monomer system may be changed to 30 parts by weight of tertiary-butyl methacrylate, 30 parts by weight of ethyl methacrylate and 40 parts by weight of triethylene glycol dimethacrylate.

EXAMPLE 13

The procedure of Example 1 may be repeated and the liquid monomer system may be 30 parts by weight of phenyl methacrylate, 30 parts by weight of ethyl methacrylate and 40 parts by weight of triethylene glycol dimethacrylate.

EXAMPLE 14

Example 1 may be repeated and the liquid monomer system may be changed to 30 parts by weight of 3,3,5-trimethylcyclohexyl methacrylate, 30 parts by weight of ethyl methacrylate and 40 parts by weight of triethylene glycol dimethacrylate.

EXAMPLE 15

Example 1 may be repeated and the liquid monomer system may be changed to 30 parts by weight of styrene, 30 parts by weight of methyl methacrylate and 40 parts by weight of triethylene glycol dimethacrylate.

EXAMPLE 16

The results of wear life tests and compressive strength for the polymerized compositions of Examples 1 through 8 are reported in the following Table:

TABLE I

| Example | Wear Test Results (hours/mil) | Compressive Strength (thousands of lbs per sq. inch) |
|---|---|---|
| 1 | 249 | 36 |
| 2 | 217 | 29 |
| 3 | 208 | 22 |
| 4 | 310 | 22 |
| 5 | 242 | 17 |
| 6 | 223 | 26 |
| 7 | 275 | 34 |
| 8* | 57 | 38 |

*Comparative

We claim:

1. Composition useful for preparing permanent dental restorations having high compressive strength, wear resistance and a coefficient of friction of not greater than 0.3 comprising:
   (a) about 10 to 60 parts by weight of a liquid monomer system comprised of one or more monoethylenically unsaturated monomers and about 10% to 80% by weight, based on said liquid monomer system, of one or more polyethylenically unsaturated crosslinking monomers, said monomer system, containing at least 70%, by weight of said monomer system, of acrylic monomer;
   (b) about 40 to 90 parts by weight of a mixture of (1) organic polymeric particulate substance insoluble in said liquid monomer system selected from the class consisting of poly(ethylene-co-chlorotrifluoroethylene), poly(vinylidene fluoride), nylon and polyacetal and (2) inorganic particulate substance insoluble in said liquid monomer system wherein the weight ratio of the organic particulate substance to inorganic particulate substance is from about 2:1 to about 10:1; and
   (c) a free radical initiator system.

2. A composition according to claim 1 wherein at least about 97 percent, by weight of the total inorganic particulate substance has a Moh hardness of up to about 5.

3. A composition according to claim 1 wherein said monoethylenically unsaturated monomer is methyl methacrylate.

4. A composition according to claim 1 wherein said monoethylenically unsaturated monomer or monomers are selected from the group consisting of those having glass transition temperatures of about 50° to about 120° C. if polymerized in the absence of said polyethylenically unsaturated monomer.

5. A composition according to claim 4 wherein said glass transition temperature is from about 65° to about 110° C.

6. A composition according to claim 1 wherein said mixture of (1) organic polymeric particulate substance and (2) inorganic particulate substance is present in an amount of from about 50 to about 70 parts by weight.

7. A composition according to claim 1 wherein said inorganic particulate substance has an average particle diameter of from about 0.1 micron to about 75 microns.

8. A composition according to claim 1 wherein said inorganic particulate substance is selected from the group consisting of calcium hydroxyapatite, calcium carbonate, stearate coated calcium carbonate, calcium metasilicate, talc, clay, calcium sulfate, quartz, silica, glass beads, glass fibers, and combinations thereof.

9. A composition according to claim 1 wherein the average particle diameter of said organic polymeric particulate substance is from about 0.1 micron to about 75 microns.

10. A composition according to claim 1 wherein said free radical initiator system is a redox initiator system.

11. A composition according to claim 1 wherein said free radical initiator system is a photochemical initiator system.

12. A composition according to claim 1 wherein said free radical initiator system is a peroxydicarbonate activated system.

13. A composition according to claim 10 wherein said redox initiator system is a combination of benzoyl peroxide and an aromatic amine.

14. A composition according to claim 1 wherein said polyethylenically unsaturated monomer is a polyfunctional acrylate or methacrylate or mixtures thereof.

15. A composition according to claim 1 wherein said polyethylenically unsaturated monomer is selected from the group consisting of trimethylolpropane trimethacrylate, ethylene glycol dimethacrylate, diethylene glycol dimethacrylate, triethylene glycol dimethacrylate, poly(ethylene glycol) dimethacrylate, butylene glycol dimethacrylate, 1,6-hexanediol dimethacrylate, 1,10-decamethylene glycol dimethacrylate, butylene diacrylate, pentaerythritol tetraacrylate, bis-GMA, divinyl benzene, diallyl maleate, and ethoxylated bisphenol-A-dimethacrylate.

16. A composition according to claim 1 wherein said polyethylenically unsaturated monomer comprises about 20 to about 80%, by weight, of the liquid monomer system.

17. A composition according to claim 1 wherein up to about 80%, by weight of the inorganic particulate substance, has a Moh hardness in excess of 5.

18. A composition according to claim 1 wherein said monoethylenically unsaturated monomer is selected from the class consisting of ethyl methacrylate, octafluoropentyl methacrylate, hydroxyethyl methacrylate, hexafluoroisopropyl methacrylate, pentafluoropropyl acrylate, pentafluoropropyl methacrylate, heptafluorobutyl acrylate and heptafluorobutyl methacrylate.

19. A composition according to claim 1 further including one or more of (a) suspension polymers in bead form; (b) finely ground dental restorative resin; and (c) emulsion polymer in bead form.

20. A composition according to claim 1 wherein said free radical initiator is selected from the class consisting of thermal initiators, redox initiators and photochemical initiators and said redox initiator includes an oxidizing agent and a reducing agent and one of said agents is present in said liquid monomer system and the second agent is present in said mixture of organic particulate substance and inorganic particulate substance, and, when said free radical initiator is a thermal initiator, said thermal initiator is present in said mixture of organic particulate substance and inorganic particulate substance, and when said initiator is a photochemical initiator, said photochemical initiator is present in either the liquid monomer system or the mixture of organic particulate substance and inorganic particulate substance.

21. A permanent dental restoration having a compressive strength of at least 30,000 psi and a rotary wear value of at least 200 hours/mil made from the composition of any one of claims 1 through 16 and 18 through 20.

22. A method of making a permanent dental restoration having a compressive strength of at least 20,000 psi and a rotary wear value of at least 200 hours/mil comprising filling a mold with the composition of claim 1, allowing the composition to set, and then to cure.

23. A method of making permanent dental crowns having high compressive strength, wear resistance and a coefficient of friction of not greater than 0.3 comprising (I) mixing (a) a first component comprising about 10 to 60 parts by weight of a liquid monomer system comprised of one or more monoethylenically unsaturated monomers and about 10% to about 80% by weight, based on said liquid monomer system, of one or more polyethylenically unsaturated crosslinking monomers, said monomer system containing at least about 70%, by weight of said monomer system, of acrylic monomer, with (b) a second component comprising about 40 to 90 parts by weight of a mixture of (1) organic polymeric particulate substance insoluble in said liquid monomer system and selected from the class consisting of poly-(ethylene-co-chlorotrifluoroethylene), poly(vinylidene fluoride), nylon and polyacetal and (2) inorganic particulate substance insoluble in said liquid monomer system wherein the weight ratio of the organic particulate substance to the inorganic particulate substance is from about 2:1 to about 10:1, said mixing taking place in the presence of a free radical initiator, (II) allowing the resultant mixture to achieve a suitable viscosity, (III) filling a tooth-shaped preformed mold or impression tray with the resultant thickened mixture, and (IV) applying the filled mold or tray to the prepared tooth to which the crown is to be affixed, (V) allowing the composition to set, (VI) removing the resultant set crown from the mouth and then from the mold or impression tray, (VII) finishing and polishing the crown, (VIII) filling the crown with dental cement and placing the dental crown on the prepared tooth.

24. Composition useful for preparing permanent dental restorations having high compressive strength, resistance and a coefficient of friction of not greater than 0.3 comprising:
(a) about 25 to 60 parts, by weight, of a liquid monomer system comprised of one or more monoethylenically unsaturated monomers and about 15 to 50% by weight, based on said liquid monomer system, of a polyethylenically unsaturated crosslinking monomer;
(b) about 40 to 75 parts by weight, of a mixture of (1) organic polymeric particulate substance insoluble in said liquid monomer system and selected from the class consisting of poly(ethylene-co-chlorotrifluoroethylene), poly(vinylidene fluoride), nylon and polyacetal and (2) inorganic particulate substance insoluble in said liquid monomer system wherein the weight ratio of the organic to inorganic particulate substance is from about 2:1 to about 10:1 respectively and said inorganic particulate substance is selected from the group consisting of hydroxyapatite, calcium carbonate, stearate coated calcium carbonate, calcium sulfate, calcium metasilicate, talc, clay, and combinations thereof; and
(c) a free radical initiator system.

25. A composition according to claim 24 wherein said monoethylenically unsaturated monomers is methyl methacrylate.

26. A composition according to claim 24 wherein said inorganic particulate substance has a Moh hardness of up to about 5.

27. A composition according to claim 24 wherein up to about 3% by weight, based on the weight of inorganic particulate substance present, includes an inorganic particulate substance selected from the class consisting of glass beads, quartz, silica, glass fibers, and combinations thereof.

28. A composition according to claim 24 wherein up to about 80% by weight, based on the weight of inorganic particulate substance present, includes an inorganic particulate substance selected from the class consisting of glass beads, quartz, silica, glass fibers and combinations thereof.

* * * * *